United States Patent [19]  [11]  4,219,672
Borggrefe  [45]  Aug. 26, 1980

[54] ETHER CARBOXYLIC ACIDS

[75] Inventor: Gerhard Borggrefe, Dusseldorf, Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 221,815

[22] Filed: Jan. 28, 1972

[30] Foreign Application Priority Data

Feb. 3, 1971 [DE] Fed. Rep. of Germany ....... 2104976

[51] Int. Cl.$^2$ ............................................. C07C 59/12
[52] U.S. Cl. .............................. 562/583; 260/501.17; 260/501.1
[58] Field of Search ............ 260/535 P, 501.1, 501.17; 562/583

[56] References Cited

U.S. PATENT DOCUMENTS 3,725,290  4/1973  Nelson et al. .................... 260/535 P Primary Examiner—Paul J. Killos
Attorney, Agent, or Firm—Hammond & Littell, Weissenberger & Muserlian

[57] ABSTRACT

Novel ethercarboxylic acids and their salts containing at least two carboxylic acids and at least one glycolic acid ether, useful as sequestering agents for alkaline earth metal ions, as well as a process for their preparation.

6 Claims, No Drawings

ETHER CARBOXYLIC ACIDS

THE PRIOR ART

Organic polycarboxylic acids having nitrogen or phosphorus atoms are known as sequestering agents for metal ions. Inorganic acids such as the polyphosphates are also known as sequestering agents for metal ions. These conventional sequestering agents, however, have become suspect as increasing the nitrogen and phosphorus content of waste waters leading to an imbalance in the ecology.

OBJECTS OF THE INVENTION

An object of the present invention is the development of compounds capable of sequestering metal ions, particularly alkaline earth metal ions, which compounds on degradation in waste waters do not give rise to nitrogen or phosphorus containing compounds. Another object of the present invention is the development of ethercarboxylic acid compounds having a formula selected from the group consisting of $$CH_2-O-CH_2-COOMe$$
$$|$$
$$CH_2-O-CH_2-COOMe,$$

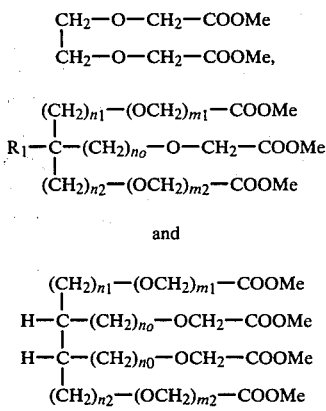

and $$(CH_2)_{n1}-(OCH_2)_{m1}-COOMe$$
$$|$$
$$H-C-(CH_2)_{no}-OCH_2-COOMe$$
$$|$$
$$H-C-(CH_2)_{n0}-OCH_2-COOMe$$
$$|$$
$$(CH_2)_{n2}-(OCH_2)_{m2}-COOMe$$

wherein $R_1$ represents a member selected from the group consisting of hydrogen, alkyl having from 1 to 2 carbon atoms, COOMe and $-(CH_2)_{n3}-OCH_2-COOMe$; Me represents a member selected from the group consisting of hydrogen, an alkali metal and $N(R_2)$ where $R_2$ represents a member selected from the group consisting of hydrogen, lower alkyl and lower alkylol; and $n_o$, $n_1$, $n_2$, $m_3$, $m_1$ and $m_2$ are integers from 0 to 1; with the proviso that the carbon atom bonded to $R_1$ has at most only one direct bond to an oxygen and when $R_1=H$ and $n_o=0$, the carbon atom bonded to $R_1$ is bonded to two identical groups.

A yet further object of the present invention is the development of a process for the production of said ethercarboxylic acids by reacting a corresponding hydroxy compound with an ester of a diazoacid in the presence of a Lewis acid catalyst and saponifying the resulting ester of an ethercarboxylic acid.

These and other objects of the present invention will become more apparent as the description thereof proceeds.

DESCRIPTION OF THE INVENTION

The above objects have been achieved by the development of polycarboxylic ethercarboxylic acids of the general formula:

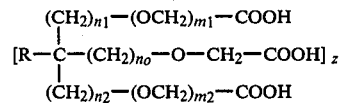

$$[R-C-(CH_2)_{no}-O-CH_2-COOH]_z$$

(with upper and lower branches $(CH_2)_{n1}-(OCH_2)_{m1}-COOH$ and $(CH_2)_{n2}-(OCH_2)_{m2}-COOH$)

wherein R represents a hydrogen atom, an alkyl with 1 to 2 carbon atoms or another $-(CH_2)_{n1}-(OCH_2)_{m1}-COOH$ group, z is 0, 1 or 2 and $n_o$, $n_1$, $n_2$, $m_1$, $m_2$ are 0 or 1, with the restriction that the carbon atom, bound to R, has at most only one direct bond to oxygen, at least one $-OCH_2-COOH-$ group exists in the molecule and for $R=H$, $z=1$, $n_o=0$ the central carbon atom is bound to two identical groups. These acids may be utilized per se or in the form of their salts capable of sequestering alkaline earth metal ions. More particularly, the invention relates to ethercarboxylic acid compounds having a formula selected from the group consisting of $$CH_2-O-CH_2-COOMe$$
$$|$$
$$CH_2-O-CH_2-COOMe,$$

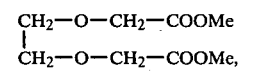

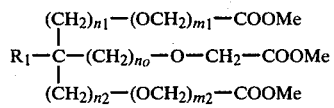

and

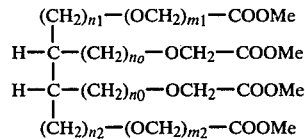

wherein $R_1$ represents a member selected from the group consisting of hydrogen, alkyl having from 1 to 2 carbon atoms, COOMe and $-(CH_2)_{n3}-OCH_2-COOMe$; Me represents a member selected from the group consisting of hydrogen, an alkali metal and $N(R_2)$ were $R_2$ represents a member selected from the group consisting of hydrogen, lower alkyl and lower alkylol; and $n_o$, $n_1$, $n_2$, $m_3$, $m_1$ and $m_2$ are integers from 0 to 1; with the proviso that the carbon atom bonded to $R_1$ has at most only one direct bond to an oxygen and when $R_1=H$ and $n_o=0$, the carbon atom bonded to $R_1$ is bonded to two identical groups.

Representatives of the compounds, according to the invention, are the following:

bis-O-carboxymethyl-glycol, tris-O-carboxymethyl-glycerine, O-carboxymethyl-tartronic acid, bis-O-carboxymethyl-tartaric acid, O-carboxymethyl-citric acid, tris-O-carboxymethyl-1,1,1-trimethylolpropane, tris-O-carboxymethyl-1,1,1-trimethylolethane, bis-o-carboxymethyl-glyceric acid.

A preferred process for the preparation of the invention compounds is characterized in that compounds of the general formulae $$HO-CH_2-CH_2-OH,$$

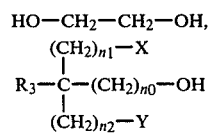

and

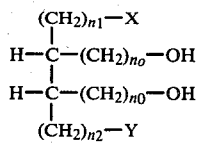

wherein $R_3$ represents a member selected from the group consisting of hydrogen, alkyl having from 1 to 2 carbon atoms, methylol and X; X and Y represent a member selected from the group consisting of hydroxyl and —COOR; where R is lower alkyl; and $n_o$, $n_1$ and $n_2$ are integers from 0 to 1; with the proviso that the carbon atom bonded to $R_3$ has at most only one direct bond to an oxygen and where $R_3$=H, and $n_o$=0, the carbon atom bonded to $R_3$ is bonded to two identical groups; are reacted with a diazoacetic acid ester, preferably a lower alkyl ester, in the presence of a Lewis acid catalyst, saponifying the resulting ethercarboxylic acid ester and recovering the desired ethercarboxylic acid compounds.

Among the starting compounds of the above formula are, for example, ethylene glycol, glycerine, lower alkyl esters of tartronic acid, citric acid, tartaric acid, glyceric acid, particularly the methyl and ethyl esters, as well as other alkanepolyols such as 1,1,1-trimethylolethane, 1,1,1-trimethylolpropane, pentaerythritol, etc.

Among the diazoacetic acid esters, particularly the lower alkyl esters and primarily the ethyl ester, is utilized in the synthesis.

The O-alkylation of the above-named starting substances is generally carried out at temperatures from −20° C. to 0° C. in the presence of Lewis acids, particularly of boron trifluoride in the form of an ether complex. From 0.5% to 5% of the catalyst, based on the hydroxyl group containing compound, are usually employed. Diazoacetic ester is added in an excess, which appropriately should be from 10% to 20% above the stoichiometrically required amount.

The reaction may be carried out without solvents, if the starting substances are present at the reaction temperature as liquids. If the solids are reacted, substances may be used as solvents which are inert under the reaction conditions, particularly the lower chlorinated hydrocarbons such as chloroform.

For working up of the reaction mixture, first water is added and the reaction products are extracted with a water-insoluble solvent. From the separated organic phase the reaction product is isolated by distillation.

The saponification of the reaction products may be done in a conventional way, for instance with 10% to 20% aqueous NaOH solution, whose amount is to be calculated so, that a 10% to 20% excess above the stoichiometrically required amount is present. The free ethercarboxylic acids are advantageously obtained from the resulting saponification solutions by passing the same through a strongly acidic cation exchanger, such as Lewatit S-100, and the eluate is concentrated under reduced pressure.

The substances, according to the invention, are usable per se or in the form of their salts as sequestering agents, particularly for calcium ions.

The salts are preferably the alkali metal salts, such as the sodium or potassium salts, the ammonium salts, or the amine salts with lower alkylamines such as mono-, di-, or tri-methyl- or ehtyl-amine, or with lower alkylolamines such as mono- or di-ethanol or propanol-amine. Partial salts of alkaline earth metals which still retain sufficient carboxy groups to sequester further alkaline earth metal ions may also be employed.

The corresponding complexes are stable over a wide pH-range. Such sequestering agents, free of N and P have the advantage in not having any nourishing effect on the flora of natural waters.

The following specific examples are illustrative of the invention without being deemed limitative in any respect.

EXAMPLE 1

Tris-O-carboxymethyl-glycerine (a) Tris-O-carbethoxymethyl-glycerine 3 gm of freshly distilled $BF_3$-ether complex were added to 138.13 gm (1.5 mol) of anhydrous glycerine and excess of diazoacetic acid ethyl ester (591.6 gm=5.2 mol) was added dropwise with constant stirring at a temperature of from −10° C. to 0° C.

After the nitrogen evolution ended, the reaction mixture was treated with water and the aqueous phase extracted with ether. The ether layer was separated, combined with the organic phase, washed until neutral, dried over $Na_2SO_4$ and subsequently concentrated.

The residue remaining was distilled under a high vacuum. The fractions distilling in the range of 174° to 185° C./0.1 mm ($n_D^{20}$=1.4459 to 1.4469) were 90% to 97% pure, according to the gas chromatograms. A redistillation gave a main fraction having a boiling point of 164° to 167° C./0.05 mm ($n_D^{20}$=1.4460) with a purity of 97%. Yield 200.5 gm.

The repeated distillation resulted in a pure product, according to gas chromatography.

b.p. 162° to 167° C./0.01 mm.

$n_D^{20}$=1.4460.

Yield: 184 gm (35% of theoretical).

Mass spectrum: m/e=350 (molecule mass).

Analysis: $C_{15}H_{26}O_9$ (350.37): Calc.: C, 51.42%; H, 7.48%; O, 41.10%; Sap. No. 480. Found: C, 51.17%; H, 7.53%; O, 41.26%; Sap. No. 477.

IR-spectrum (film).

Ester-CO=1750 cm$^{-1}$ (5.71μ).

(b) Tri-O-carboxymethyl-glycerine 60 gm (0.17 mol) of tris-O-carbethoxymethyl-glycerine were suspended in a solution of 28.8 gm (0.62 mol) of NaOH in water, and the solution was heated at reflux until homogenized (about ¾ hour). Then it was lead through a cation exchange (Lewatit S-100) and the eluate concentrated at reduced pressure.

A colorless oil remained which formed after longer drying over $P_2O_5$ at 60° C. a colorless half-solid, strongly hygroscopic mass of tris-O-carboxymethyl-glycerine.

Yield: 41.3 gm (91.5% of theoretical).

Water by Karl Fischer: 0.96% $H_2O$.

Mass spectrum: m/e=267 (molecule mass+1 proton).

Analysis: $C_9H_{14}O_9$ (266.2): Calc.: C, 40.61%; H, 5.30%; O, 54.09%; Acid No. 632. Found: C, 40.22%; H, 5.32%; O, 53.91%; Acid No. 628.

EXAMPLE 2

Tris-O-carboxymethyl-1,1,1-trimethylolpropane (a) Tris-O-carbethoxymethyl-1,1,1-trimethylol-propane A sludge of 134.2 gm (1 mol) of trimethylpropane in 500 ml of $CHCl_3$ was treated with 7.05 gm of $BF_3$-ether complex. An excess of diazoacetic acid ethyl ester (376.5 gm=3.3 mol) was added dropwise slowly at a temperature of from $-20°$ to $-10°$ C. to this suspension. With $N_2$ evolution, gradually homogenization occurred.

After the first violent $N_2$ evolution was ended, the mixture was kept a few more hours under ice-cooling and subsequently the solution was poured onto ice.

The chloroform phase was separated and washed until neutral, dried, concentrated and the remaining residue distilled in high vacuo.

The fractions distilling in the range of 174° to 198° C./0.1 to 0.2 mm($n_D^{20}$=1.4505 to 1.4513) were twice redistilled. A colorless oil of a boiling point of 172° to 173° C./0.02 mm was recovered.

$n_D^{20}$=1.4501.

Yield: 121.3 gm(31% of the theoretical).

The compound was found pure by gas chromatography.

Mass spectrum: m/e=392 molecule mass.

Analysis: $C_{18}H_{32}O_9$ (392.45): Calc.: C, 55.09%; H, 8.22%; O, 36.69%. Found: C, 55.22%; H, 8.45%; O, 36.74%.

IR-spectrum (film).

Ester-CO=1754 cm$^{-1}$ (5.7$\mu$).

(b) tris-O-carboxymethyl-1,1,1-trimethylolpropane 50 gm (0.23 mol) of tris-O-carbethoxymethyl-trimethylolpropane was added to a solution of 30 gm (0.75 mol) of NaOH in water. After 3-hour heating at reflux, homogenization occurred. The alkaline solution was lead through a cation exchanger (Lewatit S-100) and the eluate concentrated under reduced pressure. A colorless oily residue of tris-O-carboxymethyl-1,1,1-trimethylolpropane remained. It was dried at room temperature under vacuum over $P_2O_5$ and slowly crystallization took place. Colorless crystals of m.p. 102° to 104° C. were obtained.

Yield: 39.9 gm.

Water by Karl Fischer: 4.96% $H_2O$.

A sample was dried under vacuum for a longer time over $P_2O_5$ to give a product having a melting point of 102° to 104° C.

Mass spectrum: m/e=309 (molecule mass+1 proton).

Analysis $C_{12}H_{20}O_9$ (308.29): Calc.: C, 46.75%; H, 6.54%; O, 46.71%; Acid No. 545.92. Found: C, 46.79%; H, 6.43%; O, 46.94%; Acid No. 545.92.

EXAMPLE 3

Bis-o-carboxymethyl-glyceric acid 125.4 gm (1.1 mol) of diazoacetic acid ethyl ester were added dropwise with constant stirring to a solution of 60 gm (0.5 mol) glyceric acid methylester and 2 ml $BF_3$-ether complex in 150 ml of $CHCl_3$, the temperature being kept at $-20°$ C.

After the vigorous nitrogen evolution ended, 200 ml $CHCl_3$ were added and the resulting solution washed until neutral, dried over $Na_2SO_4$ and subsequently concentrated.

The residue remaining was distilled twice under a high vacuum. The resulting product had a boiling point of 136°–142° C./0.1 mm ($n_D^{20}$=1.4445).

Yeild: 65.1 gm (44.5% of theoretical).

Analysis: $C_{12}H_{20}O_8$ (292.29): Calc.: C, 49.31%; H, 6.90%; O, 43.79%. Found: C, 49.11%; H, 7.11%; O, 43.84%.

The product was treated in a manner analogous to Example 1 to yield the respective free acid.

I claim:

1. An ethercarboxylic acid compound selected from the group consisting of (1) a compound selected from the group consisting of O-carboxymethyl-citric acid, tris-O-carboxymethyl-1,1,1-trimethylolpropane, tris-O-carboxymethyl-1,1,1-trimethylolethane and bis-O-carboxymethyl-glyceric acid; and (2) a salt of said compound selected from the group consisting of alkali metal salts, ammonium salts, lower alkylamine salts, lower alkylolamine salts and the mixtures thereof.

2. The ethercarboxylic acid compound of claim 1, which is selected from the group consisting of (1) a compound selected from the group consisting of O-carboxymethyl-citric acid, and bis-O-carboxymethyl-glyceric acid; and (2) a salt of said compound selected from the group consisting of alkali metal salts, ammonium salts, lower alkylamine salts, lower alkylolamine salts and the mixtures thereof.

3. O-carboxymethyl-citric acid.

4. Tris-O-carboxymethyl-1,1,1-trimethylol-ethane.

5. Bis-O-carboxymethyl-glyceric acid.

6. Tris-O-carboxymethyl-1,1,1-trimethylolpropane.

* * * * *